(12) United States Patent
Phillips et al.

(10) Patent No.: US 11,309,080 B2
(45) Date of Patent: Apr. 19, 2022

(54) SYSTEM FOR MONITORING COMPLIANT USAGE OF NEGATIVE PRESSURE WOUND THERAPY

(71) Applicant: KCI Licensing, Inc., San Antonio, TX (US)

(72) Inventors: Gregory Phillips, Broken Arrow, OK (US); Brian Robey, Fair Oaks Ranch, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1652 days.

(21) Appl. No.: 14/882,403

(22) Filed: Oct. 13, 2015

(65) Prior Publication Data

US 2016/0184497 A1    Jun. 30, 2016

Related U.S. Application Data

(60) Provisional application No. 62/063,457, filed on Oct. 14, 2014.

(51) Int. Cl.
*A61M 35/00* (2006.01)
*A61M 1/00* (2006.01)
(Continued)

(52) U.S. Cl.
CPC ............ *G16H 40/67* (2018.01); *A61M 1/734* (2021.05); *A61M 1/86* (2021.05); *A61M 1/90* (2021.05); *G16H 10/60* (2018.01); *G16H 15/00* (2018.01); *G16H 20/10* (2018.01); *G16H 40/20* (2018.01); *G16H 40/63* (2018.01);
(Continued)

(58) Field of Classification Search
CPC .......... A61M 35/00; A61M 1/00; A61M 3/00; A61M 31/00; A61M 2205/15; A61M 2205/18; A61M 2205/3553; A61M 2205/3576; A61M 2205/3592;
(Continued)

(56) References Cited

U.S. PATENT DOCUMENTS 1,355,846 A    10/1920   Rannells
2,547,758 A    4/1951   Kelling
(Continued)

FOREIGN PATENT DOCUMENTS

AU     550575 B2    3/1986
AU     745271 B2    3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.
(Continued)

*Primary Examiner* — Michele M Kidwell
*Assistant Examiner* — Ilya Y Treyger

(57) ABSTRACT

Systems, methods, and apparatuses for treating a tissue site are described. In some embodiments, the system may include a dressing, a negative-pressure source, and a communication device. The communication device may be coupled to the negative-pressure source and configured to transmit operational data of the negative pressure source to a remote location for monitoring usage of the system.

8 Claims, 5 Drawing Sheets

(51) Int. Cl.
*G16H 40/67* (2018.01)
*G16H 40/20* (2018.01)
*G16H 15/00* (2018.01)
*G16H 40/63* (2018.01)
*G16H 10/60* (2018.01)
*G16H 20/10* (2018.01)
*A61M 3/00* (2006.01)
*A61M 31/00* (2006.01)
*A61F 13/00* (2006.01)
*A61F 13/02* (2006.01)
*G16H 20/40* (2018.01)

(52) U.S. Cl.
CPC ..... *A61M 2205/15* (2013.01); *A61M 2205/18* (2013.01); *A61M 2205/3553* (2013.01); *A61M 2205/3576* (2013.01); *A61M 2205/3584* (2013.01); *A61M 2205/3592* (2013.01); *A61M 2205/505* (2013.01); *A61M 2205/52* (2013.01); *G16H 20/40* (2018.01)

(58) Field of Classification Search
CPC ......... A61M 2205/505; A61M 2205/52; A61F 13/00; A61F 13/02; A61F 8/44
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,997,476 A | 12/1999 | Brown |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,334,778 B1 | 1/2002 | Brown |
| 6,345,623 B1 | 2/2002 | Heaton et al. |
| 6,368,273 B1 | 4/2002 | Brown |
| 6,488,643 B1 | 12/2002 | Tumey et al. |
| 6,493,568 B1 | 12/2002 | Bell et al. |
| 6,553,998 B2 | 4/2003 | Heaton et al. |
| 6,612,985 B2 | 9/2003 | Eiffert et al. |
| 6,814,079 B2 | 11/2004 | Heaton et al. |
| 6,968,375 B1 | 11/2005 | Brown |
| 7,223,235 B2 | 5/2007 | Brown |
| 7,223,236 B2 | 5/2007 | Brown |
| 7,516,192 B2 | 4/2009 | Brown |
| 7,587,469 B2 | 9/2009 | Brown |
| 7,769,605 B2 | 8/2010 | Brown |
| 7,840,420 B2 | 11/2010 | Brown |
| 7,846,141 B2 | 12/2010 | Weston |
| 7,870,249 B2 | 1/2011 | Brown |
| 7,921,186 B2 | 4/2011 | Brown |
| 7,991,625 B2 | 8/2011 | Rosenfeld et al. |
| 8,062,273 B2 | 11/2011 | Weston |
| 8,140,663 B2 | 3/2012 | Brown |
| 8,175,895 B2 | 5/2012 | Rosenfeld et al. |
| 8,216,198 B2 | 7/2012 | Heagle et al. |
| 8,251,979 B2 | 8/2012 | Malhi |
| 8,257,327 B2 | 9/2012 | Blott et al. |
| 8,277,378 B2 | 10/2012 | Bardy |
| 8,326,649 B2 | 12/2012 | Rosenfeld |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |

(56) References Cited

U.S. PATENT DOCUMENTS

| | | | |
|---|---|---|---|
| 8,568,386 B2 | 10/2013 | Malhi | |
| 8,672,917 B2 | 3/2014 | Sigg et al. | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0002299 A1 | 1/2010 | Karpowicz et al. | |
| 2011/0009295 A1 | 4/2011 | Jacobs | |
| 2011/0092958 A1 | 4/2011 | Jacobs | |
| 2014/0001863 A1 | 1/2014 | Bennett et al. | |
| 2014/0163491 A1 | 6/2014 | Schuessler et al. | |
| 2014/0298928 A1* | 10/2014 | Duesterhoft | A61F 13/00051 73/865.8 |
| 2015/0080788 A1 | 3/2015 | Blott et al. | |
| 2015/0133829 A1 | 5/2015 | DeBusk et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2197789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2010011920 A2 | 1/2010 |
| WO | 2012/078784 A1 | 6/2012 |
| WO | 2014151930 A2 | 9/2014 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Appiication PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page Engiish translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R, Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
European Examination Report for corresponding Application No. 157913963, dated Mar. 21, 2018.
International Search Report and Written Opinion for corresponding PCT Application No. PCT/US2015/055398 dated Jan. 26, 2016.
Japanese Notice of Rejection for corresponding Application No. 2017-519554, dated Nov. 2, 2011.

\* cited by examiner

SYSTEM FOR MONITORING COMPLIANT USAGE OF NEGATIVE PRESSURE WOUND THERAPY

TECHNICAL FIELD

This disclosure relates generally to medical treatment systems for treating tissue sites and monitoring the usage of such systems. More particularly, but not by way of limitation, the disclosure relates to a system for monitoring the compliant usage of negative-pressure wound therapy systems.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "negative-pressure therapy," but is also known by other names, including "negative-pressure wound therapy," "reduced-pressure wound therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, development and operation of reduced-pressure systems, components, and processes continues to present significant challenges to manufacturers, healthcare providers, and patients.

If a patient undergoing negative-pressure wound therapy does not use negative-pressure systems in accordance with prescribed treatment plans, the outcomes of therapy may be less effective than desired. Currently, there is a lack of a real-time way of collecting such usage data for monitoring compliance with therapy protocols.

BRIEF SUMMARY

According to an illustrative embodiment, a system for monitoring treatment of a tissue site may include a dressing, a negative-pressure source, and a communication device. The dressing may be adapted for placing on the tissue site. The negative-pressure source may be fluidly coupled to the dressing. The communication device may be coupled to the negative-pressure source and configured to transmit operational data of the negative-pressure source.

According to another illustrative embodiment, an apparatus for treating a tissue site may include a negative-pressure source and a communication device. The negative-pressure source may be adapted to be in fluid communication with the tissue site. The communication device may be coupled to the negative-pressure source and configured to transmit operational data of the negative-pressure source.

According to yet another illustrative embodiment, a method for treating a tissue site may include applying a dressing to the tissue site, coupling a negative-pressure source to the dressing, applying negative pressure to the dressing, and transmitting operational data related to the application of the negative pressure.

Other objects, features, and advantages of the embodiments described herein will become apparent with reference to the drawings and detailed description that follow.

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
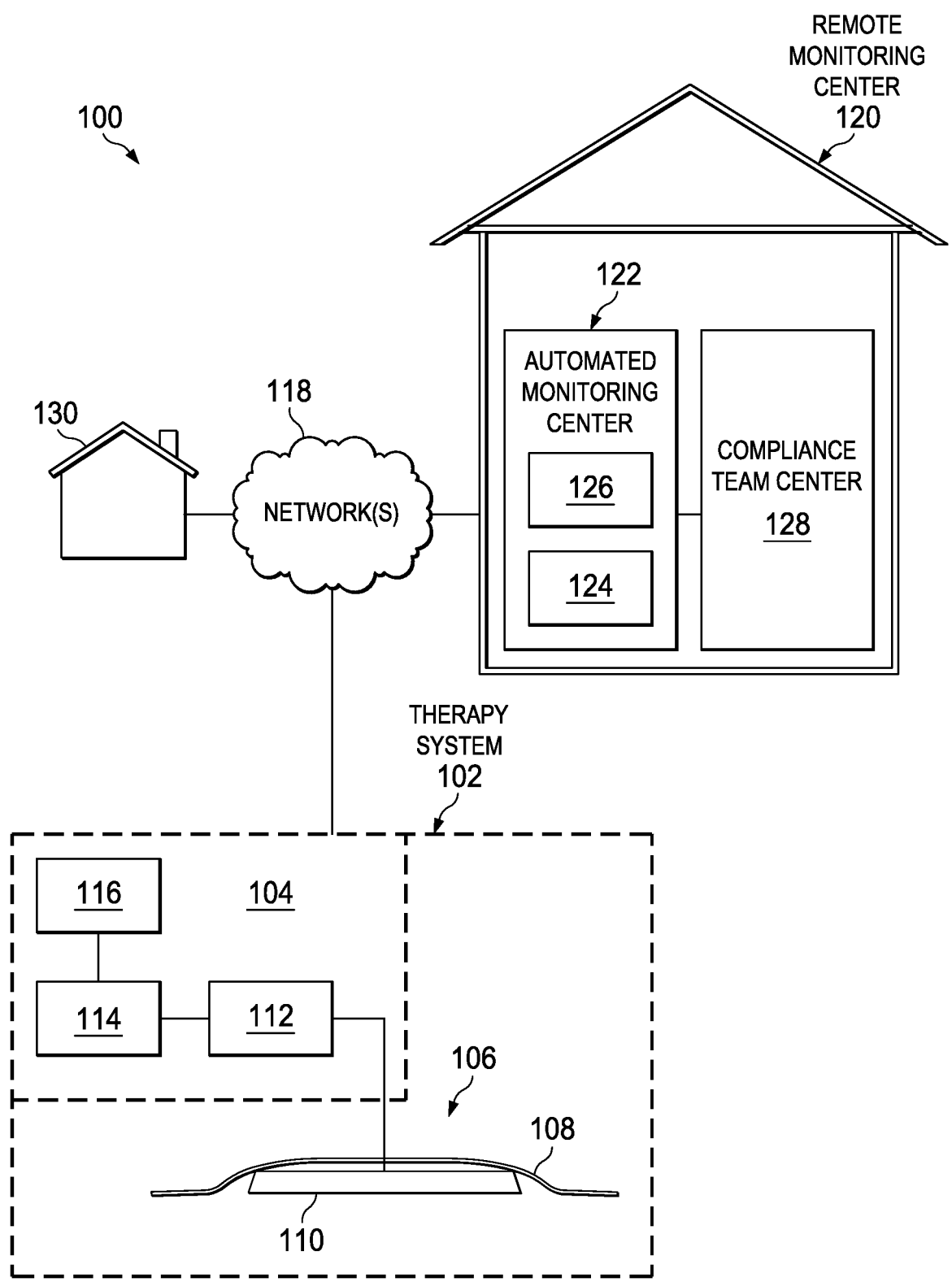
FIG. 1 is an illustration of a therapy network in accordance with an exemplary embodiment.

FIG. 1 is a schematic diagram of an example embodiment of a therapy network 100 that can provide monitored wound therapy in accordance with this specification. The therapy network 100 may include a therapy system 102, which may include a therapy unit 104 and a dressing 106. The dressing 106 may include a cover 108 and a tissue interface 110. The dressing 106 may be fluidly coupled to a negative-pressure source 114, as illustrated in FIG. 1. The therapy unit 104 may also include an exudate container, such as a container 112, fluidly coupled to the dressing 106 and to the negative-pressure source 114.

The therapy system 102 may also include a communication device 116. For example, the communication device 116 may be electrically coupled to the therapy unit 104, or in some embodiments, may be part of the therapy unit 104. The communication device 116 may be connected to the therapy unit 104 by a wire or wirelessly. The communication device 116 of the therapy system 102 may be configured to communicate with one or more networks 118 of the therapy network 100, and may include a transmitter. In one preferred embodiment, the communication device 116 may include a cellular modem and may be configured to communicate with the network(s) 118 through a cellular connection. In other embodiments, the communication device 116 may include a Bluetooth® radio, ZigBee® radio, or other wireless radio technology for communicating with the network(s) 118 through a personal area network (PAN) or a wide personal area network (WPAN). The communication device 116 may be configured to transmit data related to the operation of the therapy system 102, which may occur at a patient's home or at a treatment center, such as a hospital or physician's office.

In some embodiments, the communication device 116 may be integrated within the housing of the negative-pressure source 114 of the therapy unit 104. In other embodiments, the communication device may be separately attached to the external surface of the negative-pressure source 114, and may include a receiver configured to receive data related to the operation of the negative-pressure source 114. In one embodiment, the communication device 116 may be attached to the external surface of the negative-pressure source 114 and may be connected to the negative-pressure source 114 through a serial communication interface.

In some embodiments, the communication device 116 may include a processor that is configured with an algorithm for processing the data related to the operation of the therapy system 102, and more specifically, the negative-pressure source 114. The processor algorithm(s) may be programmed to compute usage statistics based on the usage time and conditions of the negative-pressure source 114. For example, the processor may compute the total operation time of the negative-pressure source 114 since a given patient has begun treatment, as well as compute average daily operation time(s). The processor may be configured to calculate how an average daily operation time compares with a prescribed therapy protocol and to compute a level of compliance with the corresponding prescribed therapy protocol. Additionally, the processor may be configured to generate an alert signal based on the level of compliance with the prescribed therapy protocol, which may be communicated through a network, such as network 118, by a transmitter of the communication device 116.

The therapy network 100 may also include a remote monitoring center 120 that may be in communication with the therapy system 102 through network(s) 118. For example, the communication device 116 of the therapy system 102 may be configured to transmit data through network(s) 118 to the remote monitoring center 120. The remote monitoring center 120 may include an automated monitoring center 122. The automated monitoring center 122 may include a communication center 124 as well as an alert center 126. The communication center 124 may be designed to monitor the communication links between therapy systems, such as therapy system 102, and the remote monitoring center 120. In some embodiments, the communication center 124 may include a receiving unit configured to receive data related to the operation of the therapy system 102, and more specifically the therapy unit 104 and the negative-pressure source 114. The receiving unit may include a processing device loaded with software algorithms for processing the data related to the operation of the therapy system 102 and for providing output calculations for comparing how the data related to the operation of the therapy system 102 compares to one or more threshold values. For example, in some embodiments, the threshold values may correspond to treatment protocols that prescribe a specific minimum amount of use of the therapy unit 104.

The alert center 126 of the automated monitoring center 122 may be configured to receive alert notifications communicated from the therapy systems, such as therapy system 102, as well as from the communication center 124. In some cases, the communication center 124 and/or the alert center 126 may be operated by one or more automated computers. The remote monitoring center 120 may also include a compliance team center 128. The compliance team center 128 may function as a service center for compliance staff, clinicians, or other personnel for monitoring usage of treatment systems, such as treatment system 102, by patients, as well as send alert notifications that may be escalated from the alert center 126.

The therapy network 100 may also include other entities that may communicate with therapy systems and remote monitoring centers through network(s) 118. For example, the therapy network 100 may include a third party 130. For example, the third party 130 may be an insurer. In one embodiment, the third party 130 may communicate through network(s) 118 with the remote monitoring center 120 in order to acquire usage data related to the therapy system 102. In other embodiments, the third party 130 may be able to receive usage data directly from a therapy system through network(s) 118, without needing to communicate with a therapy system.

In general, components of the therapy system 102 may be coupled directly or indirectly, and in some cases, may be detachably coupled. For example, negative-pressure source 114 may be directly coupled to container 112 and indirectly coupled to dressing 106 through container 112. Components may be fluidly coupled to each other to provide a path for transferring fluids (i.e., liquid and/or gas) between the components.

In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 106 can provide a sealed therapeutic environment proximate to a tissue site, substantially isolated from the external environment, and the negative-pressure source 114 can reduce the pressure in the sealed therapeutic environment. Negative pressure applied to a tissue site through the tissue interface 110 in the sealed therapeutic environment can induce macro-strain and micro-strain in the tissue site, as well as remove exudates and other fluids from the tissue site, which can be collected in the container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art.

In general, exudates and other fluids flow toward lower pressure along a fluid path. Thus, the term "downstream" typically implies something in a fluid path relatively closer to a source of negative pressure or further away from a source of positive pressure; conversely, the term "upstream" implies something relatively further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components herein.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by dressing 106. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 114, may be a reservoir of air at a negative pressure, or may be a manual or electrically-powered device that can reduced the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate reduced-pressure therapy. While the amount and nature of negative pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with a tissue site. If a tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site. For example, a manifold may be adapted to receive negative pressure from a source and distribute negative pressure through multiple apertures across a tissue site, which may have the effect of collecting fluid from across a tissue site and drawing the fluid toward the source. In some embodiments, though, a manifold may also facilitate delivering fluids to a tissue site, if the fluid path is reversed or a secondary fluid path is provided, for example.

In some illustrative embodiments, the pathways may be interconnected to improve distribution or collection of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In some illustrative embodiments, a manifold may be a porous foam material having interconnected cells or pores adapted to distribute negative pressure across a tissue site. The foam material may be either hydrophobic or hydrophilic. In one non-limiting example, the tissue interface 110 may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an impermeable or semi-permeable, elastomeric material that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or the entire cover 108. In some embodiments, for example, some or all of the cover 108 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

Figure 2:
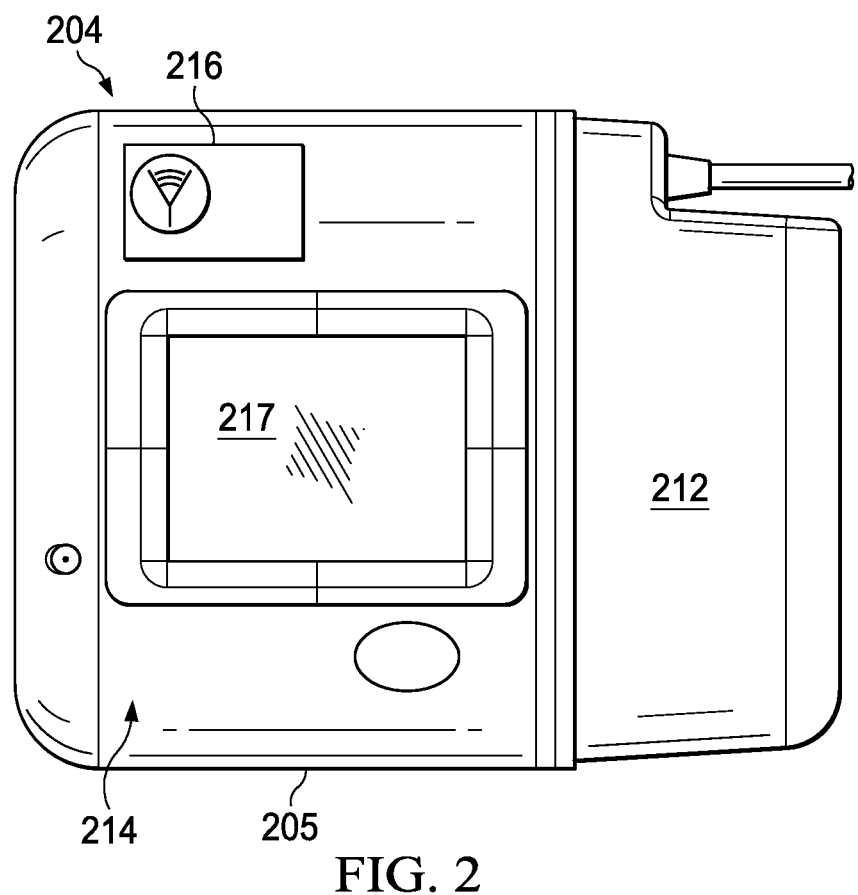
FIG. 2 is a perspective view illustrating additional details that may be associated with some example embodiments of a therapy unit in the therapy network of FIG. 1.

Referring to FIG. 2, depicted is an illustrative example of a therapy unit 204 according to one embodiment, and may be another embodiment of the therapy unit 104. Therapy unit 204 is suitable for use as a component of the therapy system 102. The therapy unit 204 may include a housing 205, which may enclose a negative-pressure source 214 and a communication device 216. The therapy unit may also include an electronic display 217 for interfacing with a user. A container 212 may be configured to attach to the housing 205 of the therapy unit 204.

Figure 3:
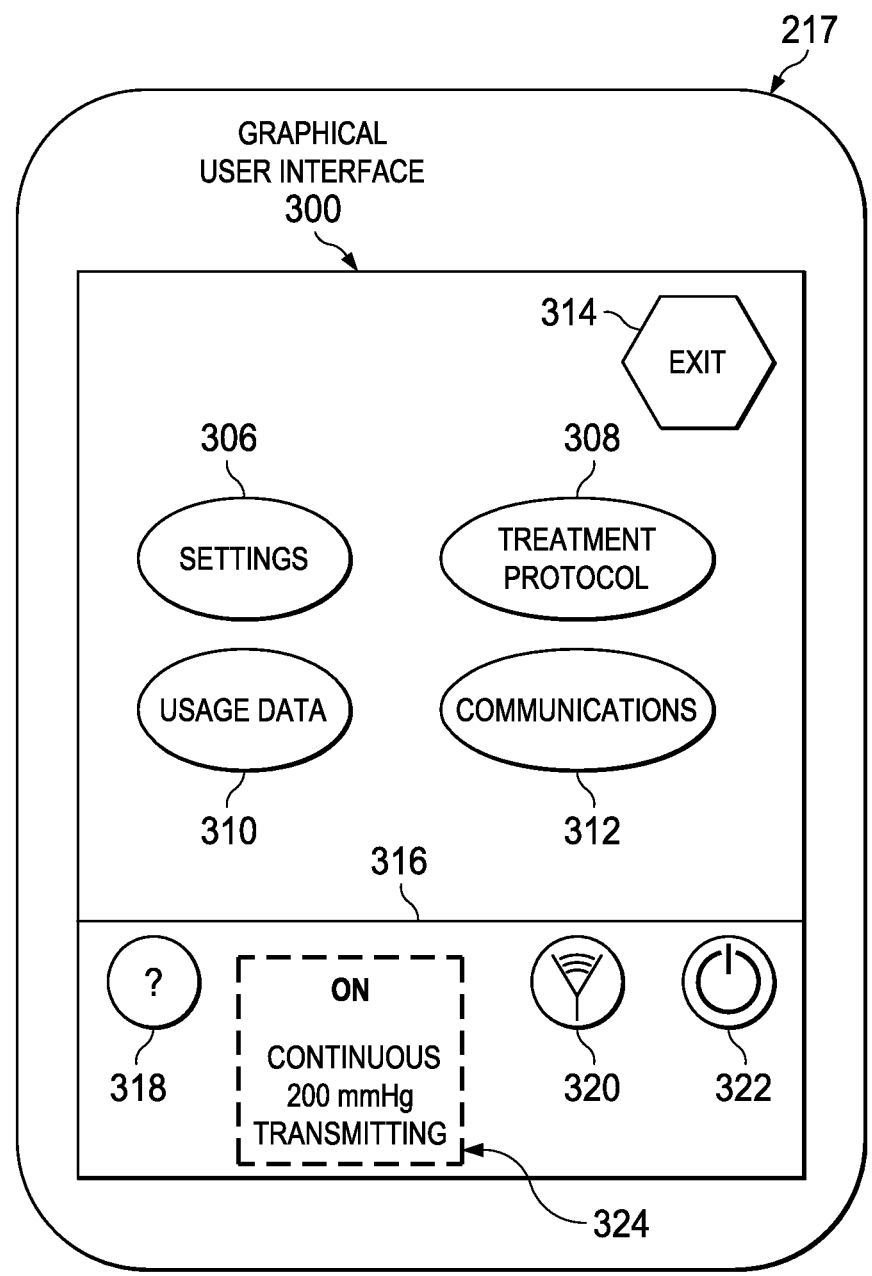
FIG. 3 illustrates a screen shot of a graphical user interface (GUI) of a therapy unit electronic display, according to an exemplary embodiment.

Referring to FIG. 3, an example embodiment of the electronic display 217 of the therapy unit 204 is shown. The electronic display 217 may be configured to display a graphical user interface (GUI) 300. The GUI 300 may include a number of selectable graphical elements, including a "settings" soft-button 306, "treatment protocol" soft-button 308, "usage data" soft-button 310, and "communications" soft-button 312, along with soft-buttons assigned to any other features related to the treatment of a tissue site. A user may select any of these functions (i.e., settings, wound type, treatment protocol, usage data, communications) to cause the electronic display 217 to present the user with another graphical user interface for performing the selected function. In addition, an "exit" soft-button 314 may be available to the user to exit the current GUI 300. It should be understood that the GUI 300 is exemplary and that other and/or alternative functions and selection elements may be provided to the user.

An information region 316 on the GUI 300 may include selectable graphical elements and display other information in which the user may be interested. For example, a "help" soft-button 318 may be displayed to enable the user to receive help about the therapy unit 204 or particular functions currently being displayed on the GUI 300. A "transmit" soft-button 320 may enable a user to selectively activate or deactivate the communication device 216 of the therapy system 102 to begin or cease transmitting usage data to the network(s) 118. An "on-off" soft-button 322 may enable a user to selectively turn the therapy unit 204 on and off. Information status region 324 may notify the user of current status of the therapy unit 204. For example, the information status region 324 may indicate that the therapy unit 204 is (i) currently on, (ii) operating according to a specifically-selected treatment protocol, and (iii) transmitting operational data to remote receiver. The information status region 324 may also indicate whether the communication device 216 is (i) currently activated, (ii) currently deactivated, (iii) currently transmitting data, and (iv) currently receiving data. The information status region 324 may also provide a visual indication of the compliance level of a patient's usage of the therapy system 102 with a prescribed treatment protocol.

In some embodiments, the therapy system 102 may be configured to display usage compliance information on the information status region 324 for the user, or to notify a caregiver or other service provider, that the user, such as a patient, is complying with a prescribed treatment protocol. For example, usage compliance information may include information or data regarding whether or not negative pressure therapy is being applied to the tissue site over time. Usage compliance information also may include information or data regarding a therapy event log tracking, for example, whether the therapy system 102 is turned on or off over time. Additional compliance analysis may include information or data regarding whether or not the therapy system 102 is being utilized in compliance with a prescribed treatment protocol such as, for example, a protocol defining different pressures and/or flow rates over time. Compliance analysis may also include information or data regarding wound healing progress over time. Additional compliance output information may include output data and information such as, for example, information providing an audible or visual alert when non-compliance reaches an unacceptable level or threshold. Such output compliance information also may provide feedback to the user, such as a patient, before providing such information to others, such as clinicians, so that the user has an opportunity and is motivated to correct a non-compliant situation before reaching an unacceptable level or threshold. Additional compliance input information may include input data and information such as, for example, information regarding the settings or caregiver input entered into the therapy system 102. Such input compliance information may include, for example, therapeutic pressure settings, maximum and minimum target pressures, flow rate settings, the intensity and/or duration of any complementary treatment such as instillation of fluids, and data indicating whether negative-pressure treatment is being applied in a continuous or intermittent mode of operation.

The information status region 324 may also be configured to display messages communicated from a remote party to the user. For example, a clinician at the remote monitoring center 120 may send messages through network(s) 118 to the therapy system 102 for display to a patient. Such messages may include instructions to keep the therapy system 102 turned on and utilized. Additionally, such messages may include instructions for troubleshooting one or more issues presented with the therapy system 102. Troubleshooting instructions may include directions to empty or change an exudate container or recharge or replace a battery of the treatment system 102.

Figure 4:
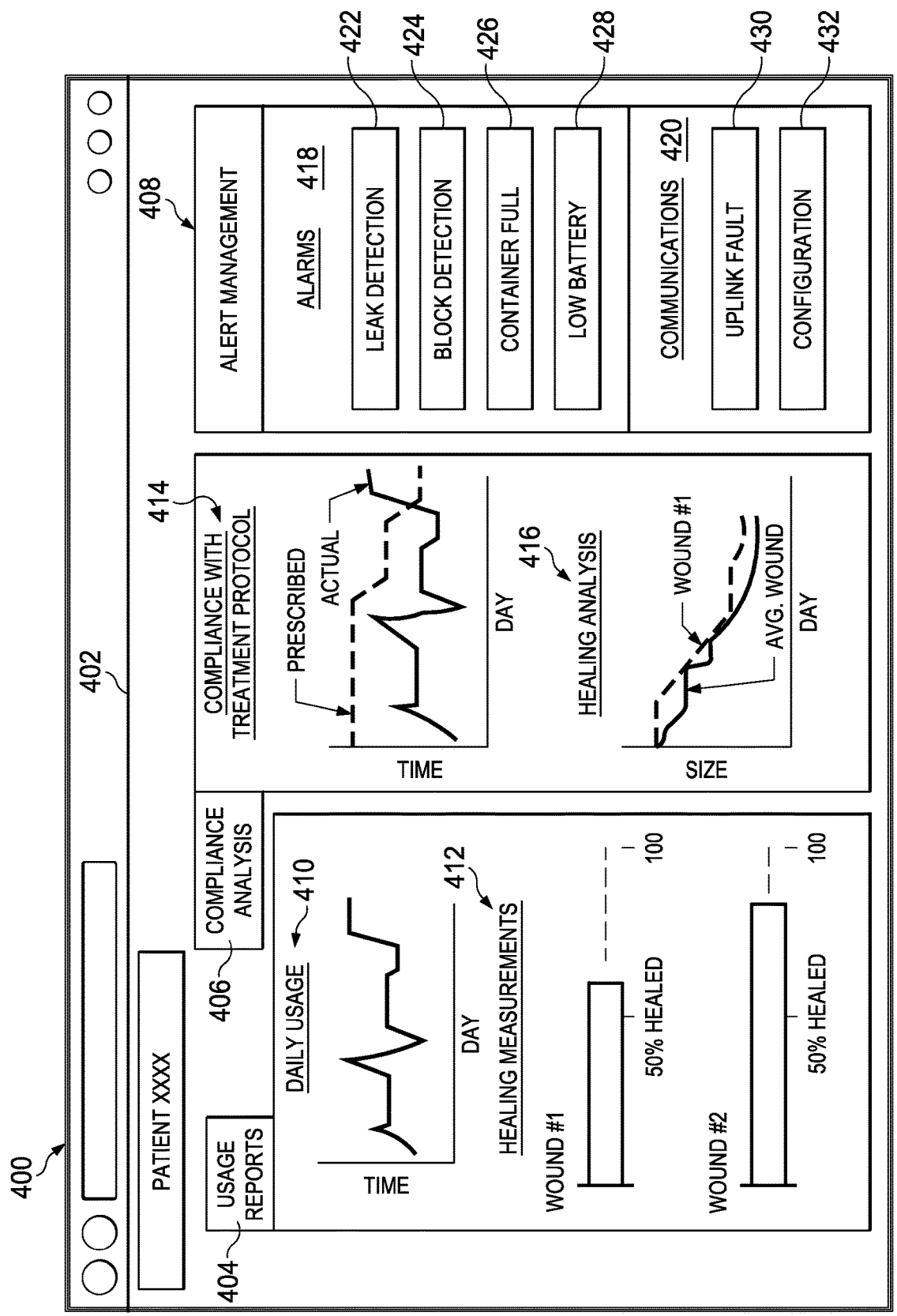
FIG. 4 illustrates a screen shot of a graphical user interface (GUI) of a usage monitoring software for operation on an electronic device, according to an exemplary embodiment.

FIG. 4 shows a screen shot of an illustrative GUI 400 of an exemplary embodiment of usage-monitoring software, or another embodiment of the GUI 300 or a portion of the GUI 300, for use on an electronic device, such as a computer having an electronic display, which may be the electronic display 217 that includes the GUI 300. This exemplary embodiment of GUI 400 provides a patient summary view 402, which includes usage compliance information embodied in a usage reports display 404, a compliance analysis display 406, and compliance output information embodied in an alert management display 408. The usage reports display 404 may correspond to usage data regarding a patient's therapy system, such as therapy system 102. The patient summary view 402 may display information based on data from device log data of a therapy system. The device log data is interpreted and manipulated by the usage-monitoring software in preparation for display. The usage-monitoring software may parse the date- and time-stamped data to calculate potential non-compliant use statistics.

The usage reports display 404 may include a daily usage summary 410, which may display to a user the total amount of time per day that a therapy system is running. The usage reports display 404 may also include a healing measurements display 412. The healing measurements display 412 may provide data for tracking the healing progression of one or more wounds of a patient. For example, the healing measurements display 412 may display data corresponding to the percentage of healing that a specific wound has undergone. Additionally, or alternatively, the healing measurements display 412 may display data relating to physical measurements of one or more wounds, such as length, width, depth, circumference dimensions, as well as others.

The compliance analysis display 406 may display data and analysis related to a patient's usage of a therapy system, such as therapy system 102, and how this usage complies with one or more treatment protocol(s). For example, compliance chart 414 may display a comparison of the amount of time a patient uses a therapy system each day versus the amount of time prescribed according to a treatment protocol. The compliance analysis display 406 may also include a healing analysis chart 416, which may compare the rate of healing of one or more wounds of a patient to average healing times for similar wound(s). Alternatively, the compliance analysis display 406 may display analysis related to the particular timeframe(s) during days or nights when a therapy system is used. The compliance analysis display 406 may also, or alternatively, display statistics related to any other aspects of a patient's usage of a therapy system or the healing of one or more wound(s).

The alert management display 408 may display information related to different types of alarms or warnings associated with the use of a treatment system, such as treatment system 102. For example, the alert management display 408 may include an alarms window 418 and a communications window 420. The alarms window 418 may include one or more indicators related to different features or functionalities of a therapy system. For example, the alarms window 418 may include a leak detection indicator 422, which may signal a user that a fluid leak has been detected on the patient's therapy system. The alarms window 418 may also include a block detection indicator 424, which may alert a user that a fluid blockage has been detected by the therapy system. A container full indicator 426, which indicates that a container for collecting wound exudate is or is nearing full, may also be included. Additionally, a low battery indicator 428 may be included, for signaling that one or more batteries of a therapy system are nearing depletion. Furthermore, the alert management display 408 may allow for remotely troubleshooting issues with the therapy system 102.

The communications window 420 of the alert management display 408 may display alerts to a user regarding the connection status with one or more therapy systems, as well as provide a user interface for viewing and changing settings related to communicating with the therapy system(s). For example, the communications window 420 may include an uplink fault indicator 430, which may signal to a user that a communication link with a therapy system being monitored has been interrupted. A configuration button 432 may also be included for allowing a user to access a menu for configuring the communications and/or network settings for establishing and maintaining remote monitoring functionality of a therapy system.

While the illustrative GUI 400 of FIG. 4 is focused on individual patient data, other illustrative GUIs may include reports focused on summary data for a broad base of patients. For example, an overview of a given patient population could be provided, which may provide for efficient identification of patient outliers who may require intercession. Such overviews may include viewing patient data on a macro level, for example, by grouping patient data by patient demographics, payer groups, wound types, or comorbidities. Providing summary views of one or more patient populations may allow for better insight into patient care on a broader scale.

In the typical homecare setting, patients undergoing wound treatment are visited once every 2-3 days for wound dressing changes, at which time the clinician may assess patient compliance in following a prescribed therapy protocol. A clinician may use the GUI 404 and its features described above of the therapy system 102 and/or additionally visually inspect the tissue site in order to make such assessment. However, visiting a patient once every 2-3 days is not optimal timing for determining whether patients have been using a negative-pressure therapy system as prescribed (e.g., for the recommended number of therapy hours per day). In many cases, providers and insurers expect that patients are using the negative-pressure therapy system 24 hours per day, however actual use by some patients may be much lower. Lacking any way to collect this usage data, the extent of the compliance issue is largely unknown. Non-compliance below certain thresholds is now understood to have an effect on patient healing.

As disclosed herein, the therapy network 100 improves the administration of negative-pressure wound therapy. For example, by providing a system for remotely monitoring usage compliance of a negative-pressure therapy system, noncompliant usage could be more quickly detected so that caregivers and patients can be more quickly advised to utilize the therapy systems as prescribed. As a result, increased compliance with treatment protocols could be achieved and faster healing of tissue sites could be accomplished. For example, a clinical care team or a home-health nurse may be able to contact a monitored patient to provide instructions for becoming compliant with a given prescribed treatment.

Figure 5:
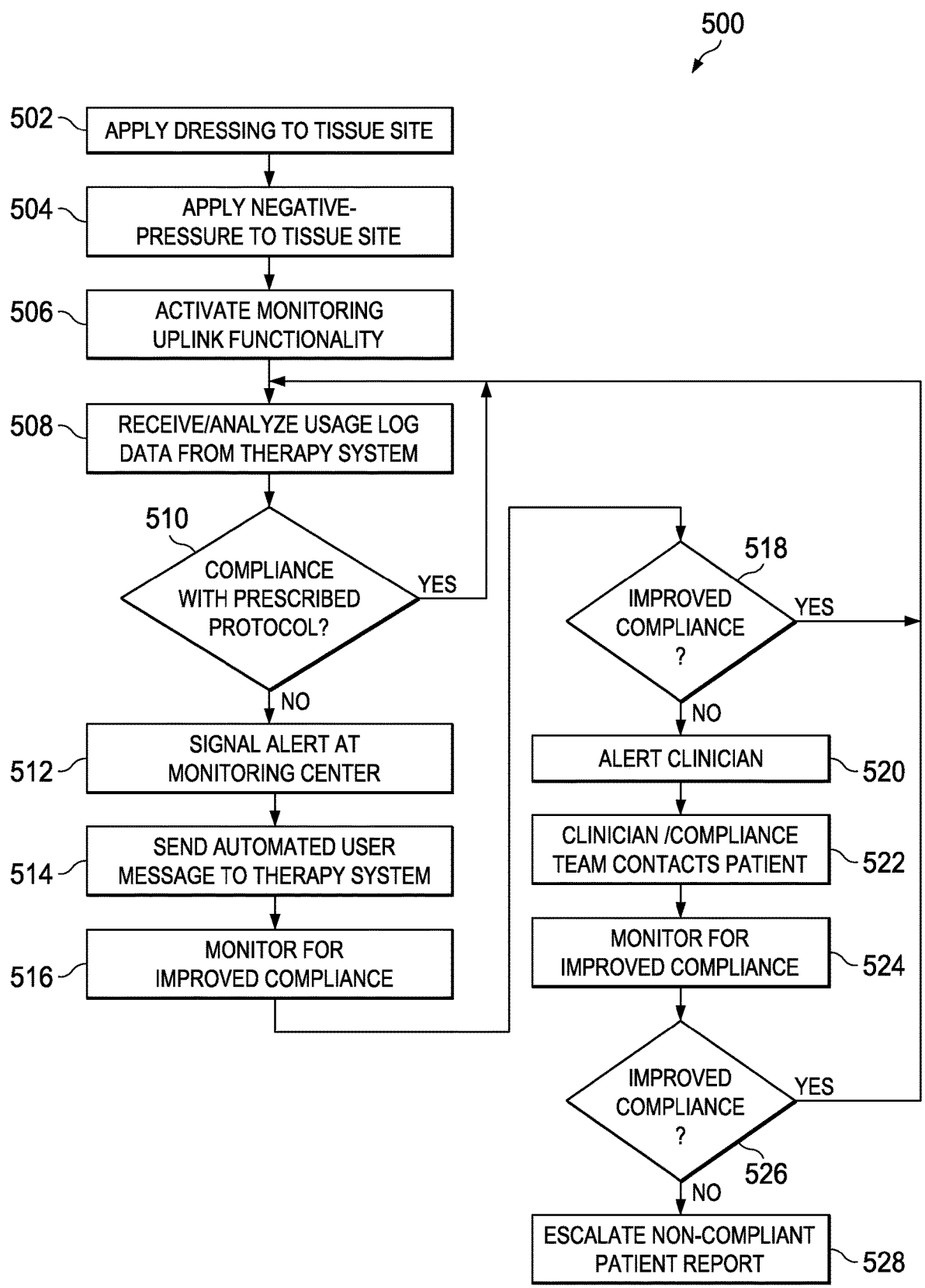
FIG. 5 is a flow diagram of an exemplary process for monitoring the usage of a wound treatment system.

In operation, the therapy network 100 and its various components and features may be used in accordance with the exemplary embodiment of a monitoring method 500 illustrated in FIG. 5. For example, operation of the therapy network 100 may begin with initiating operation of a therapy system, such as the therapy system 102. A dressing, such as dressing 106 of therapy system 102, may be applied to a tissue site, as shown in step 502. Negative pressure may then be applied to the dressing and tissue site, by fluidly connecting a negative-pressure source, such as negative-pressure source 114, to the dressing and then activating the negative-pressure source, as illustrated in step 504. Step 506 provides the process of activating the communications capability of a therapy system, and establishing communication with one or more remote monitoring centers in order to begin transmitting data, such as usage data.

Once a therapy system has begun transmitting data, usage data may be received and analyzed at a remote location, such as a remote monitoring center, as indicated in step 508. A user, for example a clinician or a compliance team member, located at a remote location may review usage data that is transmitted from a therapy system related to a specific patient by using a GUI. In some instances, the GUI may be viewed on a computing device, such as a desktop terminal. In other instances, the GUI may be viewed on a personal wireless device, such as a smartphone, using a proprietary software application.

In some preferred embodiments, such usage data and, specifically, usage compliance information, may include when a therapy unit, such as therapy unit 204, is on or off. In other embodiments, such usage compliance information may further include whether a communication device, such as communication device 216, is activated or deactivated during a given time period, and or furthermore, whether the communication device 216 is transmitting data to a remote receiver when activated. Additionally, the usage compliance information received may be analyzed to determine whether it complies with the desired usage data to be transmitted.

Upon reviewing such usage compliance information, the user may make a determination of whether a patient's usage of a therapy system is in compliance with one or more prescribed protocol(s), as illustrated in step 510. In some embodiments, an automated monitoring capability may be employed, and this determination of compliance may be made automatically. If the compliance assessment determines that the patient's therapy system is being used according to a given prescribed protocol, step 508 may be repeated according to a routine monitoring schedule. In the alternative, should the compliance assessment performed in step 510 indicate that a patient's therapy system is not being used according to a prescribed treatment protocol, an alert may be signaled at a remote monitoring center, as shown in step 512.

For example, if a patient who has been prescribed 24 hours/day of negative-pressure therapy for a wound is only using the negative-pressure treatment system for approximately 14 hours/day, the remote monitoring center may detect this discrepancy between prescribed and actual treatments. In some preferred embodiments, threshold alerts may be set for when usage compliance of negative-pressure therapy falls below an amount of time between 16 hours/day to 20 hours/day depending on other therapeutic factors and wound conditions. For instance, the input compliance threshold may be set at 18 hours/day if the compliance team decides that the present therapy is generating high amounts of wound exudate volumes may be impeding the healing process. In another example, the input compliance threshold may be set at 16 hours/day to accommodate the administration of fluid instillation therapy. In any of the embodiments, the alert threshold limits may be adjusted to account for other factors that may affect the administration of negative-pressure therapy.

While often it is preferred that patients are administered negative-pressure therapy to a wound for as close to 24 hours/day as possible, usage compliance thresholds, such as those discussed above, may be set based on empirical data indicating that usage time is critical for wound healing progression. Wound healing progression may be measured by the percent reduction of wound volume per day, i.e., wound volume reduction. Studies generating empirical data have indicated that wound volume reduction may be enhanced by the percentage of a 24-hour day that the negative-pressure therapy is administered, i.e., usage percentage. Moreover, there may be significant differences in the wound volume reduction between certain usage percentage values, indicating which usage percentage values or ranges are thresholds to be targeted for usage compliance.

As can be seen from the data in Table 1, one critical threshold may exist between the 60-69% usage percentage range (approximately 14.5 to 16.5 hours per day) and the 70-79% usage percentage range (approximately 17 to 19 hours per day). Thus, based on this data, in order to achieve a desired wound volume reduction per day of greater than about 1.5%, a user should adhere to a negative-pressure therapy compliance threshold of at least about 70%, or about 17 hours per day, to avoid an alarm warning of non-compliance.

TABLE 1

| Usage Percentage of 24-Hour Day During Course of Therapy (%) | Wound Volume Reduction/Day (%) | Number of Patients (n = 1843) |
| --- | --- | --- |
| <50% | 1.14% | 959 |
| 50-59% | 1.26% | 377 |
| 60-69% | 1.34% | 195 |
| 70-79% | 1.61% | 127 |
| 80-89% | 1.81% | 74 |
| 90-100% | 2.14% | 111 |

In addition to an alert being signaled at the remote monitoring center, an automated user message may be initiated by the remote monitoring center and sent to the therapy system, as illustrated in step 514. For example, a user message received by the therapy system may automatically be displayed on the GUI of the therapy system. In some embodiments, a chime or other form of alert may accompany the display of message, in order to attract the attention of the user. In other embodiments, a user message may be sent by the remote monitoring center through the network to the user using other means. Some examples of other messaging forms of communication may include sending a text message to a phone number on record for a particular user. Similarly, an email may be sent to an address on file for the user. In another embodiment, an automated telephone message may be delivered to a phone number on record for a user.

Following such a message being delivered to a user, usage monitoring may continue, as shown in step 516, particularly for detecting indications of improved compliance with the treatment protocol. Step 518 illustrates that usage data may again be analyzed, similarly to the type of data analysis performed in step 510, to determine if a patient has improved his or her compliance of using a treatment system with a given treatment protocol, for example, whether a designated usage threshold, such as 20 hours/day, is being met. In some cases, the determination as to whether a designated usage threshold is being met or exceeded may be evaluated on a daily basis, or may be evaluated as an average over a multiple day period. For example, the wound volume percentage reductions per day shown in Table 1 may be determined by averaging the wound volume percentage reduction over a period of several days. Additionally, the designated usage threshold may vary over time, such as being increased or reduced from one week to another. For example, in cases where a particular tissue site has shown significant healing progress, the threshold may be reduced. However, on the other hand, in cases where healing progress is less than desired, possibly due to lack of compliance with a given treatment protocol, the designated usage threshold may be increased for a period of time.

In one embodiment, an alert is generated if usage per day falls below 14 hours. In another embodiment an alert is generated if usage per day falls below 16 hours or 18 hours or usage per day in the range of 14 hours to 22 hours. Alternatively, or additionally, an alert may be generated if the average usage over a multiday time period falls below 14 hours, 16 hours, or 18 hours or average usage in the range of 14 hours to 22 hours. For example, if usage drops below an average of 15 hours over a three day time period or if usage drops below an average of 17 hours over a three day time period.

The threshold for generating an alert may be adjusted over time. In one embodiment, the threshold is set within a first higher range, such as for example, 18 hours to 22 hours. Later the threshold may be set at a lower range, such as for example, 14 hours to 16 hours. The threshold alternatively may be adjusted based on a signal received for a user or caregiver. For example, if the system receives a signal indicating a higher risk patient, such as for example, a patient first beginning therapy, a patient with an infected wound, or a patient with one or more co-morbidities, the system will utilize a higher usage threshold. Upon the system receiving a different signal from a user or patient, the system may set a lower usage threshold. A low-risk patient signal might be received for patients who have been compliant, patients with wounds that are healing or healed sufficiently, or patients visited often by caregivers.

For example, if a signal is received indicating compliance has improved, or the system determines compliance has improved, a routine monitoring schedule of treatment system usage may be resumed, as illustrated in step 508. In the event that the analyzed usage data indicates that there has not been improved compliance with a given treatment protocol, a clinician or other compliance team member may be alerted, as shown in step 520. For example, in some embodiments, an alert may be triggered in the alert center 126 of the automated monitoring center 122 and then communicated to the compliance team center 128 of the remote monitoring center 120. Upon review of the alert, a clinician or other compliance team member may contact the patient, as shown in step 522, in an effort to improve compliance with the treatment protocol. Furthermore, patients monitored by or assigned to a given clinician may be prioritized based on the severity of non-compliance.

As used herein, usage refers to time a medical device is turned on. Alternatively, usage may mean the time when therapy is being delivered. In another aspect, usage may be measured by the time a device is delivering target therapy. For example, the signal received by the system may indicate the usage by a sensor sending a message that the device has been turned on or off, or a pump has been turned on or off. The medical device may store data about usage and then send a signal to the system indicating usage on a hourly, daily, or multi day time period.

Following such contact by a clinician or other compliance team member, compliant usage monitoring may continue as shown in step 524. Similarly, step 526 illustrates that usage data may continue to be analyzed, similarly to the type of data analysis performed in steps 510 and 518. Once again, if compliance is determined to be improved, routine monitoring of treatment system usage may be resumed, in accordance with step 508. Should compliance with a prescribed treatment protocol not be improved, an alert regarding the non-compliance may be escalated within the compliance monitoring team, as shown in step 528, so that further action may be taken to improve patient care.

The systems and methods described herein may provide significant advantages, some of which have already been mentioned. For example, current methods of monitoring patient compliance require in-person review of device event logs at a patient's bedside. Manual calculations and analysis are required to determine the amount of time of non-compliance. In some instances, in order to determine 2-3 days of device usage, a clinician could spend up to ten minutes performing the calculations and analysis, which is not practical in the modern-day health care environment. As a solution, the remote therapy network as described above provides ready access wherever the Internet is available (desktop computer, smart phone, smart tablet, etc.) for a clinician to view patient compliance information. The therapy network 100 may provide analysis of the data output in order to provide caregivers information in a meaningful format. No calculations are necessary and the clinician can be alerted to provide feedback to the patient to improve compliance when needed. Based on the data studied, it is expected that this invention will improve wound healing over standard stand-alone negative-pressure wound therapy.

The therapy network 100 may provide improved patient monitoring. For example, device log data may be viewed remotely by numerous stakeholders, which may increase the frequency of interactions with a given patient. As a result, providers may be enabled to more promptly adjust treatment protocols, which may result in reduced healing times for tissue sites, as well as overall reduced costs of treatment.

Although certain illustrative, non-limiting exemplary embodiments have been presented, various changes, substitutions, permutations, and alterations can be made without departing from the scope of the appended claims. Any feature described in connection to any one exemplary embodiment may also be applicable to any other exemplary embodiment.

Further, the steps of the methods described herein may be carried out in any suitable order, or simultaneously where appropriate.

We claim:

1. A method for treating a tissue site, comprising:
   activating a negative-pressure source configured to provide negative pressure to the tissue site;
   transmitting data related to a usage time of the negative-pressure source to a remote user;
   determining that the usage time is less than a threshold value, wherein the threshold value is in a range of 16 hours/day to 19 hours/day;
   generating an alert to signal that the usage time is less than the threshold value and to prompt the remote user to contact a user of the negative-pressure source.

2. The method of claim 1, wherein the threshold value is in a range of about 17 hours/day to 18 hours/day.

3. The method of claim 2, wherein the threshold value is about 17 hours/day.

4. The method of claim 1, wherein the usage time is an average number of hours per day from two or more days.

5. A system for monitoring negative-pressure therapy, comprising:
- a negative-pressure therapy unit;
- a dressing fluidly coupled to the negative-pressure therapy unit;
- a communication device coupled to the negative-pressure therapy unit and configured to transmit operational data of the negative-pressure therapy unit; and
- a receiving unit configured to receive operational data transmitted from the communication device, wherein the receiving unit comprises a processor configured to process the operational data to provide an output determination of whether a usage time of the negative-pressure therapy unit meets a threshold value, wherein the threshold value is in a range of 16 hours/day to 19 hours/day.

6. The system of claim 5, wherein the threshold value is in a range of about 17 hours/day to 18 hours/day.

7. The system of claim 6, wherein the threshold value is about 17 hours/day.

8. The system of claim 6, wherein the threshold value is about 18 hours/day.

* * * * *